US00PP27731P3

(12) United States Plant Patent
Van Dijk

(10) Patent No.: US PP27,731 P3
(45) Date of Patent: Feb. 28, 2017

(54) ***ANTHURIUM* PLANT NAMED 'ANTHDUXH'**

(50) Latin Name: ***Anthurium andreanum* L.**
Varietal Denomination: ANTHDUXH

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 90 days.

(21) Appl. No.: 14/545,021

(22) Filed: Mar. 17, 2015

(65) Prior Publication Data

US 2016/0278271 P1 Sep. 22, 2016

(51) Int. Cl.
*A01H 5/02* (2006.01)

(52) U.S. Cl.
USPC ..... Plt./369

(58) Field of Classification Search
USPC ..... Plt./369, 365
See application file for complete search history.

(56) References Cited

U.S. PATENT DOCUMENTS

PP20,254 P2 * 9/2009 van Dijk ..... Plt./369

OTHER PUBLICATIONS

Anthura Unlimited in Varieties 2014, *Anthurium* Cut flower & Pot plant culture, pp. 35 and 47-48.*

Information Disclosure Statement for U.S. Appl. No. 14/544,292, filed Jun. 14, 2016, one page.*

Pluto Plant Variety Database Jul. 23, 2016, retrived on Jul. 26, 2016, retrieved from the Internet at <https://www3.wipo.int/pluto/user/en/index.jsp> one page.*

Anthura *Anthurium*: Cut flower and pot plant culture, published Nov. 2014, pp. 1-3, 35, 47.

EU Community Plant Variety Rights Application No. 2013/1862, Application n°A201300730, filed Jul. 5, 2013, 7 pages.

EU Community Variety Office Official Gazette, 5.2013, Oct. 15, 2013, pp. 1-3, 29, 48, introductory 2 pages, pp. 1, 29, 48.

* cited by examiner

*Primary Examiner* — June Hwu

(74) *Attorney, Agent, or Firm* — Jondle & Associates, P.C.

(57) ABSTRACT

A new and distinct variety of *Anthurium* plant named 'ANTHDUXH' particularly characterized by having bright, shiny, cordate spathes, a light pink spadix with reddish tip, a compact plant habit and outstanding long cordate leaves, is disclosed.

3 Drawing Sheets

Genus and species: *Anthurium andreanum* L.
Variety denomination: 'ANTHDUXH'.

BACKGROUND OF THE NEW PLANT

The present invention comprises a new and distinct variety of Anthurium, botanically known as *Anthurium andreanum* L., and hereinafter referred to by the variety name 'ANTHDUXH'. The new variety originated from a hybridization made in December 2006 in Bleiswijk, The Netherlands. The female parent is a red Anthurium pot plant designated '4110-04' (unpatented), and the male parent was a red *Anthurium* plant designated '5442-01' (unpatented).

A single plant was selected in November 2008 and has been asexually reproduced repeatedly by meristem tissue culture in Bleiswijk, The Netherlands over a five-year period. The present invention has been found to retain its distinctive characteristics through successive asexual propagations.

Plant Breeder's Rights for this variety have been applied for in the European Union on Jul. 5, 2013, in China on Jan. 29, 2015 and in Taiwan on Feb. 5, 2015. 'ANTHDUXH' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Bright, shiny, cordate spathe;
2) Light pink spadix with reddish tip;
3) Compact plant habit; and
4) Outstanding long cordate leaves.

DESCRIPTION OF THE PHOTOGRAPHS

This new *Anthurium* plant is illustrated by the accompanying photographs which show the overall plant habit including blooms, buds and foliage of the plant; the colors shown are as true as can be reasonably obtained by conventional photographic procedures. The photographs are of a 25-week old plant grown in a greenhouse in Bleiswijk, The Netherlands in February 2015.

DESCRIPTION OF THE NEW VARIETY

Figure 1:
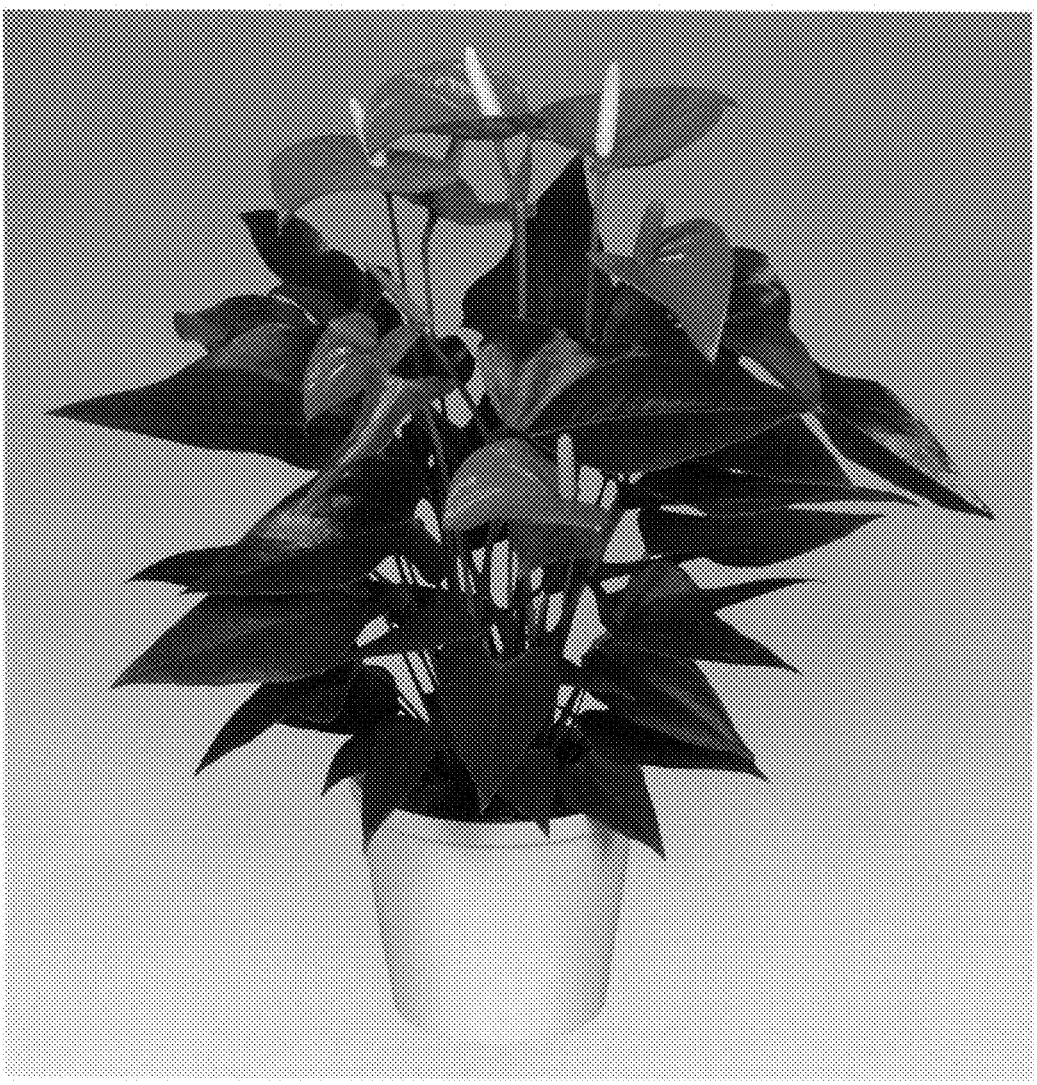
FIG. 1 shows the overall plant habit, including blooms, buds and foliage.
Figure 2:
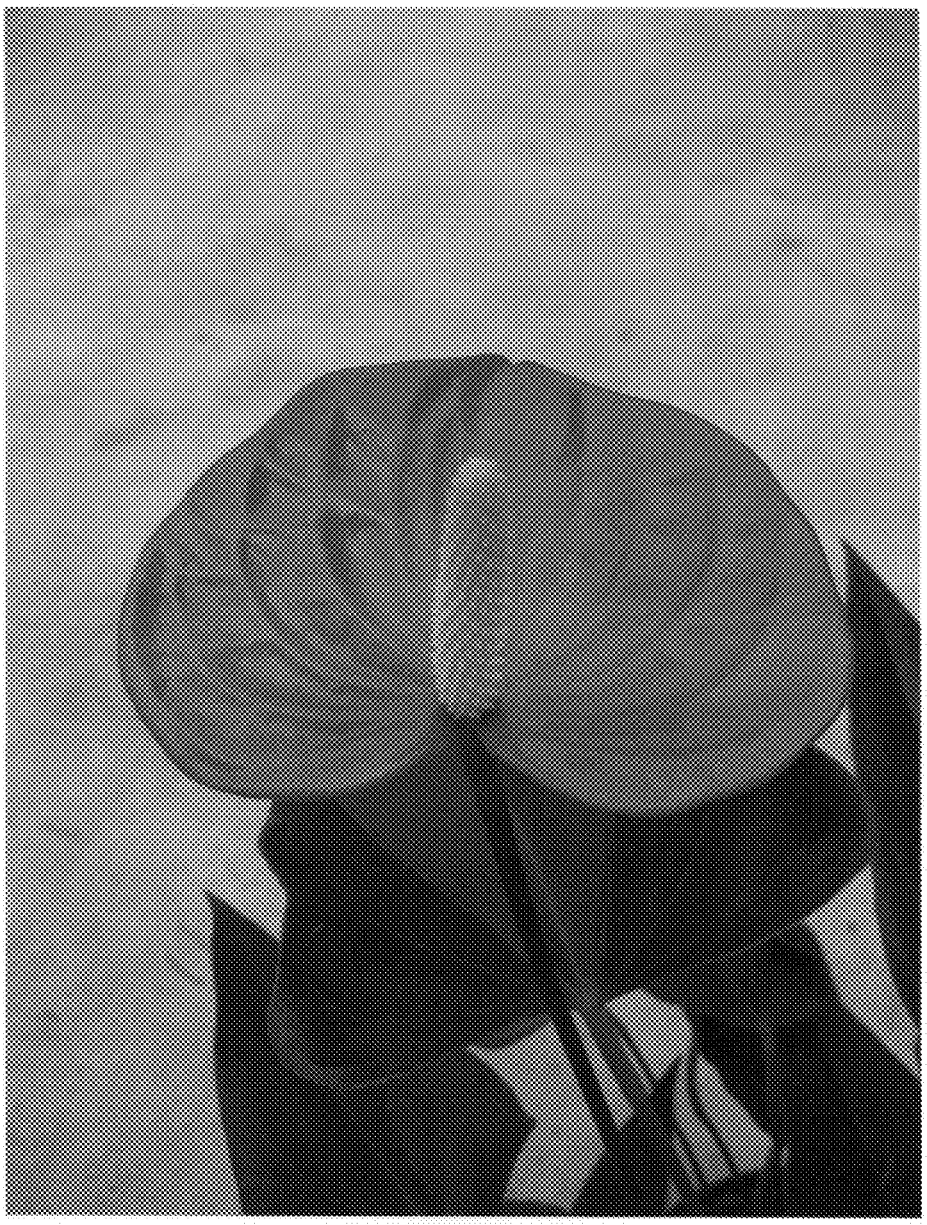
FIG. 2 shows a close-up of the mature spathe.
Figure 3:
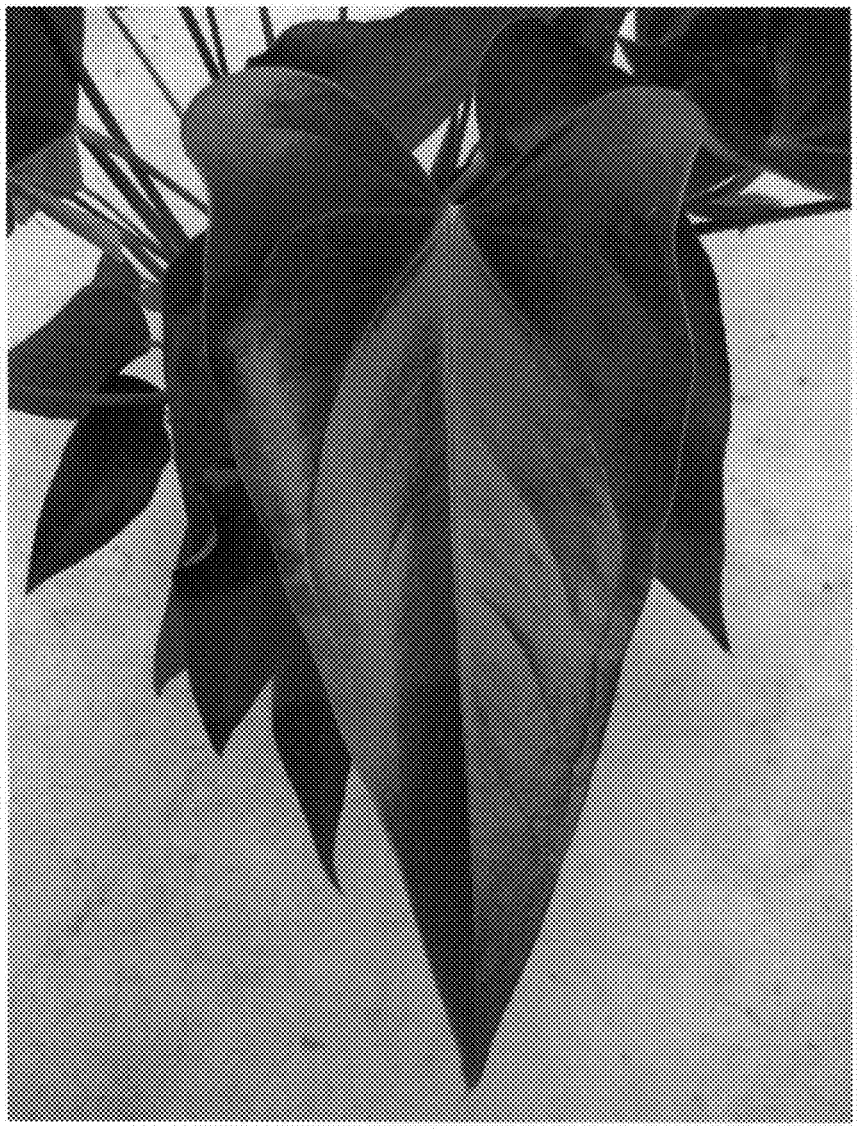
FIG. 3 shows the upper leaf blade surface.

The following detailed description sets forth the distinctive characteristics of 'ANTHDUXH'. The data which define these characteristics were collected from asexual reproductions carried out in Bleiswijk, The Netherlands. The plant history was taken on 25-week old plants which were planted from tissue culture in 14-centimeter pots and grown in a glass greenhouse between 19° C. and 24° C. Observations were made in February 2015. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family*.—Araceae.

*Botanical*.—*Anthurium andreanum* L.

*Common name*.—*Anthurium*.

*Demonimation*.—'ANTHDUXH'.

Parentage:

*Female parent*.—*Anthurium* plant '4110-04' (unpatented).

*Male parent*.—*Anthurium* plant '5442-01' (unpatented).

Plant:

*Propagation*.—Tissue culture.

*Root description*.—Fleshy pink-cream colored roots with small hairy lateral roots having yellow-colored root tips.

*Time to produce a finished flowering plant*.—30 to 35 weeks for a 14 cm pot.

*Growth habit*.—Herbaceous perennial.

*Height* (*measured from soil, including inflorescence*).—35.0 cm to 40.0 cm.

*Width* (*measured from leaf tips*).—35.0 cm to 40.0 cm.

Leaves:

*Immature leaves*.—Length: 10.0 cm to 15.0 cm. Width: 5.0 cm to 10.0 cm. Color: Upper surface: RHS 146A. Lower surface: RHS 146C. Texture (both upper and lower surfaces): Shiny. Shape: Long cordate. Base: Cordate.

*Mature leaves*.—Length (fully expanded): 16.0 cm to 20.0 cm. Width: 10.0 cm to 12.0 cm. Shape: Long cordate. Apex: Narrow acuminate. Base: Cordate. Leaf blade angle with the petiole: Between 90 degrees and 120 degrees. Leaf margin: Entire. Color: Upper surface: RHS 147B. Lower surface: RHS 146B. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS 146D.

*Lobes*.—Arrangement: Leaf blade has two small lobes extending past the petiole. The lobes are non-touching. Length of lobes of mature leaf blades: 1.0 cm to 1.5 cm. Width of lobes of mature leaf blades: 4.5 cm to 5.5 cm. Distance from petiole/leaf junction to highest point on lobes of mature leaf blades: 1.5 cm to 2.0 cm.

*Petiole*.—Cross-section: Round. Diameter: 0.2 cm to 0.3 cm. Length: 18.0 cm to 20.0 cm for a mature leaf size. Color: Mature leaf: RHS 144A. Immature leaf: RHS 144B. Cataphyl color surrounding the petiole: Outside: RHS 144B. Inside: RHS 144C.

*Geniculum*.—Length: 1.5 cm to 2.5 cm. Width: 0.3 cm to 0.4 cm. Color: RHS 144B.

Inflorescence:

*Arrangement*.—Single.

*Flowering habit* (*length of flowering season*).—Continuous.

*Number of inflorescences per plant*.—6 to 8.

*Fragrance*.—Absent.

*Longevity of inflorescence on plant*.—Over a year.

*Longevity of the flower as a cut flower*.—30 to 40 days.

Spathe:

*Buds*.—The spathe is tightly rolled around the spadix and extrudes from the peduncle sheath. After the spathe is fully open the peduncle elongates some extra centimeters.

*Arrangement*.—Spathe angle with the peduncle is between 100 degrees and 120 degrees; the spathe stands on a wiry peduncle about 7.0 cm to 9.0 cm above the foliage.

*Lobe position*.—Free.

*Shape*.—Cordate.

*Apex*.—Broad acuminate.

*Base*.—Cordate.

*Texture*.—Shiny and slightly blistered.

*Margin*.—Entire.

*Size*.—Height: 18.0 cm to 20.0 cm (peduncle length at maturity). Length: 8.0 cm to 10.0 cm. Width: 8.0 cm to 10.0 cm.

*Color*.—Just fully open: Upper surface: RHS 45A. Lower surface: RHS 45D. This red color remains approximately 35 to 40 weeks after opening. After this period the spathe is limp and dies.

Peduncle:

*Shape*.—Erect.

*Cross-section*.—Round.

*Length*.—25.0 cm to 30.0 cm.

*Diameter*.—0.3 cm to 0.4 cm.

*Color*.—RHS 146C at unrolling of spathe, slowly turning RHS 176C when the spathe matures.

Flowering time:

*General*.—One small rooted untreated tissue culture plant of 8.0 cm tall will flower after 4 to 6 months, depending on the season, and 6 to 8 blossoms will appear. More blossoms appear after some additional weeks so that a full flowering and commercial plant will have 8 to 10 red spathes. Smaller blossoms may occur on less mature plants.

Spadix:

*Size*.—Length: 3.0 cm to 4.5 cm (depending on flower size). Width (at apex): 0.6 cm to 0.7 cm. Width (at base): 0.7 cm to 0.8 cm.

*Shape*.—Columnar.

*Angle from spadix tip to peduncle*.—180 degrees.

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS 31C. Mature: RHS 36D. Ages to: RHS 144A.

Flowers:

*Quantity per spadix*.—200 to 240.

*Spadix flower arrangement*.—Bisexual, rounded in cross-section.

*Shape*.—Rounded.

*Size*.—Length: 0.05 cm to 0.1 cm. Diameter (maximum): 0.1 cm. Color: RHS 39D.

Reproductive organs:

*Stamens*.—Not visible.

*Pollen amount*.—Very few.

*Pollen color*.—RHS 156D.

*Pistil*.—Quantity: Many. Length: Less than 0.01 cm. Color: RHS 39D.

*Style*.—Not observed.

*Stigma*.—Shape: Ovoid. Diameter: Less than 0.01 cm. Color: RHS 39D.

*Ovary*.—Rarely visible.

*Ovary color*.—Not measured.

Fruit and seed set: None observed.

Disease and pest resistance: Not observed to date.

COMPARISON WITH PARENTAL AND COMMERCIAL VARIETIES

'ANTHDUXH' differs from the female parent plant '4110-04' (unpatented) in that 'ANTHDUXH' has a dark red spathe, whereas '4110-04' has a bright red spathe.

'ANTHDUXH' differs from male parent plant '5442-01' (unpatented) in that 'ANTHDUXH' has a light pink spadix with reddish tip, whereas '5442-01' has a white spadix with yellow tip.

'ANTHDUXH' differs from commercial variety 'ANTHEPEDI' (U.S. Plant Pat. No. 18,644) in that 'ANTHDUXH' has a light pink spadix with a reddish tip and long cordate leaf blade, whereas 'ANTHEPEDI' has a white spadix and cordate leaf blade. Additionally, 'ANTHDUXH' has a longer spadix than 'ANTHEPEDI'.

'ANTHDUXH' differs from commercial variety 'ANTHOLODOJ' (U.S. Plant Pat. No. 20,254) in that 'ANTHDUXH' has a light pink spadix with a reddish tip and long cordate leaf blade, whereas 'ANTHOLODOJ' has a white spadix and cordate leaf blade. Additionally, 'ANTHDUXH' has a 90 degree angle between the spadix and spathe, whereas 'ANTHOLODOJ' has a 40 to 60 degree angle between the spadix and spathe.

I claim:

1. A new and distinct variety of *Anthurium* plant named 'ANTHDUXH', substantially as illustrated and described herein.

* * * * *